(12) United States Patent  
Fan et al.

(10) Patent No.: US 7,622,705 B2
(45) Date of Patent: Nov. 24, 2009

(54) DIELECTRIC MICROCAVITY FLUOROSENSORS EXCITED WITH A BROADBAND LIGHT SOURCE

(75) Inventors: Xudong Fan, Austin, TX (US); Robert W. Wilson, Austin, TX (US); Chunmei Guo, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 11/843,917

(22) Filed: Aug. 23, 2007

(65) Prior Publication Data

US 2007/0284513 A1 Dec. 13, 2007

Related U.S. Application Data

(63) Continuation of application No. 10/854,911, filed on May 27, 2004, now Pat. No. 7,271,379.

(51) Int. Cl.
*G02B 6/42* (2006.01)
*H01J 3/14* (2006.01)
*H01J 5/16* (2006.01)

(52) U.S. Cl. .................. 250/216; 250/227.11; 372/92; 385/28

(58) Field of Classification Search ............ 250/227.11, 250/216; 372/92, 94; 385/12, 28, 30
See application file for complete search history.

(56) References Cited

U.S. PATENT DOCUMENTS

| | | | |
|---|---|---|---|
| 3,833,284 A | 9/1974 | Kaminow et al. |
| 4,715,672 A | 12/1987 | Duguay et al. |
| 4,978,187 A | 12/1990 | Minemura et al. |
| 5,077,822 A | 12/1991 | Cremer |
| 5,091,983 A | 2/1992 | Lukosz |
| 5,214,664 A | 5/1993 | Paoli |
| 5,663,790 A | 9/1997 | Ekström et al. |
| 6,219,361 B1 | 4/2001 | Guch, Jr. et al. |
| 6,389,197 B1 | 5/2002 | Iltchenko et al. |

(Continued)

FOREIGN PATENT DOCUMENTS

GB 2 293 883 4/1996

(Continued)

OTHER PUBLICATIONS

Armani, D.K., et al; "Ultra-High-Q Toroid Microcavity on a Chip", Letters to Nature, *Nature* (Feb. 27, 2003); vol. 421, Nature Publishing Group; pp. 925-928.

(Continued)

*Primary Examiner*—Kevin Pyo
(74) *Attorney, Agent, or Firm*—Robert S. Moshrefzaden

(57) ABSTRACT

A microresonator sensor apparatus has a microcavity resonator that defines equatorial whispering gallery modes (EWGMs), whose frequencies are separated by the free spectral range (FSR). The EWGMs lie in a plane perpendicular to a microcavity resonator axis. A light source is optically coupled to inject light into the microcavity resonator. The light source produces output light having an output spectrum whose bandwidth is approximately equal to or broader than the FSR of the EGWMs. One or more fluorescent materials are excited using the excitation light coupled into the microcavity resonator. A fluorescent signal arising from fluorescence of the one or more fluorescent materials is then detected.

11 Claims, 5 Drawing Sheets

U.S. PATENT DOCUMENTS

| | | | |
|---|---|---|---|
| 6,490,039 B2 | 12/2002 | Maleki et al. |
| 6,507,684 B2 | 1/2003 | Tapalian et al. |
| 6,512,866 B1 | 1/2003 | Fan et al. |
| 6,583,399 B1 | 6/2003 | Hunziker et al. |
| 6,594,425 B2 | 7/2003 | Tapalian et al. |
| 6,657,731 B2 | 12/2003 | Tapalian et al. |
| 6,665,476 B2 | 12/2003 | Braun et al. |
| 6,668,111 B2 | 12/2003 | Tapalian et al. |
| 6,777,244 B2 | 8/2004 | Pepper et al. |
| 6,781,696 B1 | 8/2004 | Rosenberger et al. |
| 6,795,481 B2 | 9/2004 | Maleki et al. |
| 6,813,285 B2 | 11/2004 | Peterson |
| 6,853,479 B1 | 2/2005 | Ilchenko et al. |
| 6,865,317 B2 | 3/2005 | Vahala et al. |
| 6,879,752 B1 | 4/2005 | Ilchenko et al. |
| 6,888,973 B2 | 5/2005 | Kolodziejski et al. |
| 6,888,987 B2 | 5/2005 | Sercel et al. |
| 6,891,996 B2 | 5/2005 | Sercel et al. |
| 6,891,997 B2 | 5/2005 | Sercel et al. |
| 6,895,135 B2 | 5/2005 | Kaneko et al. |
| 6,901,101 B2 | 5/2005 | Frick |
| 7,019,847 B1 | 3/2006 | Bearman et al. |
| 7,065,276 B2 | 6/2006 | Scheuer et al. |
| 7,091,049 B2 | 8/2006 | Boga et al. |
| 7,095,010 B2 | 8/2006 | Scherer et al. |
| 7,197,196 B2 | 3/2007 | Lin et al. |
| 7,245,801 B2 | 7/2007 | Boyd et al. |
| 7,283,707 B1 | 10/2007 | Maleki et al. |
| 7,343,067 B2 | 3/2008 | Barwicz et al. |
| 2001/0038651 A1 | 11/2001 | Maleki et al. |
| 2002/0018611 A1 | 2/2002 | Maleki et al. |
| 2002/0041730 A1 | 4/2002 | Sercel et al. |
| 2002/0044739 A1 | 4/2002 | Vahala et al. |
| 2002/0068018 A1 | 6/2002 | Pepper et al. |
| 2002/0079453 A1 | 6/2002 | Tapalian et al. |
| 2002/0094150 A1 | 7/2002 | Lim et al. |
| 2002/0097401 A1 | 7/2002 | Maleki et al. |
| 2002/0172457 A1 | 11/2002 | Tapalian et al. |
| 2002/0192680 A1 | 12/2002 | Chan et al. |
| 2003/0016907 A1 | 1/2003 | LoCascio et al. |
| 2003/0082237 A1 | 5/2003 | Cha et al. |
| 2004/0023396 A1 | 2/2004 | Boyd et al. |
| 2004/0091212 A1 | 5/2004 | Strecker et al. |
| 2004/0120638 A1 | 6/2004 | Frick |
| 2004/0146431 A1 | 7/2004 | Scherer et al. |
| 2004/0196465 A1 | 10/2004 | Arnold et al. |
| 2005/0035278 A1 | 2/2005 | Margalit et al. |
| 2005/0053319 A1 | 3/2005 | Doan |
| 2005/0074200 A1 | 4/2005 | Savchenkov et al. |
| 2005/0077513 A1 | 4/2005 | Fan et al. |
| 2005/0078731 A1 | 4/2005 | Fan et al. |
| 2005/0105868 A1 | 5/2005 | Arakida |
| 2005/0111309 A1 | 5/2005 | Peng |
| 2005/0147372 A1 | 7/2005 | Bourdelais et al. |
| 2005/0169582 A1 | 8/2005 | Tan et al. |
| 2005/0249509 A1 | 11/2005 | Nagarajan et al. |
| 2005/0263679 A1 | 12/2005 | Fan et al. |
| 2005/0265658 A1 | 12/2005 | Fan et al. |
| 2006/0110100 A1 | 5/2006 | Blauvelt et al. |
| 2006/0159392 A1 | 7/2006 | Popovic |
| 2006/0170931 A1 | 8/2006 | Guo et al. |
| 2007/0036500 A1 | 2/2007 | Suzuki et al. |
| 2007/0071386 A1* | 3/2007 | Digonnet et al. ............ 385/32 |
| 2007/0237478 A1 | 10/2007 | D'Aguanno et al. |
| 2008/0008423 A1 | 1/2008 | Scheuer et al. |

FOREIGN PATENT DOCUMENTS

| | | |
|---|---|---|
| GB | 2 387 130 | 10/2003 |
| WO | WO 2001/40757 | 6/2001 |
| WO | WO 2001/67565 | 9/2001 |
| WO | WO 2001/85341 | 11/2001 |
| WO | WO 2002/13337 | 2/2002 |
| WO | WO 2002/16986 | 2/2002 |
| WO | WO 2004/038370 | 5/2004 |

OTHER PUBLICATIONS

Blair et al., "Resonant-enhanced evanescent-wave fluorescence biosensing with cylindrical optical cavities", Applied Optics, vol. 40, No. 4, Feb. 1, 2001, pp. 570-582.

Boyd et al., "Sensitive disk resonator photonic biosensor", Applied Optics, vol. 40, No. 31, Nov. 1, 2001, pp. 5742-5747.

Burlak, G., et al; "Electromagnetic Oscillations in a Multilayer Spherical Stack", *Optics Communications* (Jun. 1, 2000); vol. 180; pp. 49-58.

Burlak, G., et al; "Electromagnetic Eigenoscillations and Fields in a Dielectric Microsphere with Multilayer Spherical Stack", *Optics Communications* (Jan. 1, 2001); vol. 187; pp. 91-105.

Burlak, G., et al; "Transmittance and Resonance Tunneling of the Optical Fields in the Microspherical Metal-Dielectric Structures", *Optics Communications* (2002); vol. 206; pp. 27-37.

Chan, S., et al. "Porous Silicon Microcavities for Biosensing Applications," *Physical Status Solid*, vol. 182, (2000) pp. 541-546.

Chan, S., et al; "Nanoscale Silicon Microcavities for Biosensing", *Materials Science & Engineering C* (2001); vol. 15; pp. 277-282.

Chan, S., et al; "Identification of Gram Negative Bacteria Using Nanoscale Silicon Microcavities", *Journal of American Chemical Society* (2001); vol. 123; pp. 11797-11798.

Coffer et al., "Strategies Toward the Development of Integrated Chemical Sensors Fabricated from Light Emitting Porous Silicon", Proceedings of the SPIE, vol. 3226, 1997, pp. 168-179.

Crisan et al., "Sol-Gel Preparation of Thin Films for Integrated Optics", $10^{th}$ International Symposium on Electron Devices for Microwave and Optoelectronic Applications, Nov. 18-19, 2002, Manchester, UK., pp. 205-210.

De Stefano, L., et al., "Optical Sensing of Flammable Substances Using Porous Silicon Microcavities," *Materials Science and Engineering*, vol. 100, Jul. 25, 2003, pp. 271-274.

Garmire, E, et al, "Propagation Losses in Metal-film-substrate Optical Waveguides", *Journal of Quantum Electronics*, vol. QE-8, No. 10, Oct. 1972, pp. 763-766.

Johnson, B.R.; "Theory of Morphology-Dependent Resonances: Shape Resonances and Width Formulas", *Journal Optical Society of America A* (Feb. 1993); vol. 10, No. 2; pp. 343-352.

Kakarantzas, G., et al; "Miniature All-Fiber Devices Based on $CO_2$ Laser Microstructuring of Tapered Fibers", *Optics Letters* (Aug. 1, 2001); vol. 26, No. 15; pp. 1137-1139.

Kaminow, I.P., et al., "Metal-Clad Optical Waveguides: Analytical and Experimental Study", *Applied Optics*, vol. 13, (1974), pp. 396-405.

Knight, J.C., et al; "Mapping Whispering-Gallery Modes in Microspheres with a Near-Field Probe", *Optics Letters* (Jul. 15, 1995); vol. 20, No. 14; pp. 1515-1517.

Krioukov, E., et al; "Integrated Optical Microcavities for Enhanced Evanescent-Wave Spectroscopy", *Optics Letters* (Sep. 1, 2002); vol. 27, No. 17; pp. 1504-1506.

Krioukov et al., "Sensor based on an integrated optical microcavity", Optics Letters, vol. 27, No. 7, Apr. 1, 2002, pp. 512-514.

Laine, J.-P., et al; "Acceleration Sensor Based on High-Q Optical Microsphere Resonator and Pedestal Antiresonant Reflecting Waveguide Coupler", *Sensors and Actuators A* (2001); vol. 93; pp. 1-7.

Laine, J.-P., et al; "Microsphere Resonator Mode Characterization by Pedestal Anti-Resonant Reflecting Waveguide Coupler", *IEEE Photonics Technology Letters* (Aug. 2000); vol. 12, No. 8; pp. 1004-1006.

Little, B.E., et al; "Pedestal Antiresonant Reflecting Waveguides for Robust Coupling to Microsphere Resonators and for Microphotonic Circuits", *Optics Letters* (Jan. 1, 2000); vol. 25, No. 1; pp. 73-75.

Luk, J.M.C., et al; "Rapid and Sensitive Detection of *Salmonella* (O : 6,7) by Immunomagnetic Monoclonal Antibody-Based Assays", *Journal of Immunological Methods* (1991); vol. 137; pp. 1-8.

Lugo, J.E., et al; "Porous Silicon Multilayer Structures: A Photonic Band Gap Analysis", *Journal of Applied Physics* (Apr. 15, 2002); vol. 91, No. 8; pp. 4966-4972.

Martin, A.L., et al; "Replica-Molded High-Q Polymer Microresonators", *Optics Letters* (Mar. 15, 2004); vol. 29, No. 6; pp. 533-535.

Mulloni, V., et al. "Porous Silicon Microcavities as Optical Chemical Sensors," *Applied Physics Letters*, vol. 76, No. 18, May 1, 2000, pp. 2523-2525.

Otto, A., et al, "Modification of the Total Reflection Modes in a Dielectric Film by One Metal Boundary", *Optics Communications*, vol. 3, No. 4, Jun. 1971, pp. 254-258.

Pettipher, G.L., et al; "Rapid Enumeration of Microorganisms in Foods by the Direct Epifluorescent Filter Technique", *Applied and Environmental Microbiology* (Oct. 1982); vol. 44, No. 4; pp. 809-813.

Pipino et al., "Evanescent wave cavity ring-down spectroscopy with a total-internal-reflection minicavity", Review of Scientific Instruments, American Institute of Physics, vol. 68, No. 8, Aug. 8, 1997, pp. 2978-2989.

Plowman, T.E., et al; "Femtomolar Sensitivity Using a Channel-Etched Thin Film Waveguide Fluoroimmunosensor", *Biosensors & Bioelectronics* (1996); Elsevier Science Ltd.; vol. 11, No. 1/2; pp. 149-160.

Popescu, A., et al; "The Gram Stain after More than a Century", *Biotechnic and Histochemistry* (1996); vol. 71, No. 3; pp. 145-151.

Reisinger, A, "Attenuation Properties of Optical Waveguides with a Metal Boundary", *Appl. Phys. Lett.*, vol. 23, No. 5, Sep. 1, 1973, pp. 237-239.

Shibata et al., "Laser Emission from Dye-Doped Organic-Inorganic Particles of Mircocavity Structure", Journal of Sol-Gel Science and Technology, vol. 8, 1997, pp. 959-964.

Spillane, S.M., et al; "Ultralow-Threshold Raman Laser Using a Spherical Dielectric Microcavity", *Nature* (Feb. 7, 2002); vol. 415; pp. 621-623.

Suematsu, et al, "Fundamental Transverse Electric Field (TE0) Mode Selection for Thin-film Asymmetric Light Guides", *Appl. Phys. Lett.*, vol. 21, No. 6, Sep. 15, 1972, pp. 291-293.

Sumetsky, M., "Whispering-Gallery-Bottle Microcavities: the Three-Dimensional Etalon", *Optics Letters* (Jan. 1, 2004); vol. 29, No. 1; pp. 8-10.

Tapalian, C., et al; "High-Q Silica Microsphere Optical Resonator Sensors Using Stripline-Pedestal Anti-Resonant Reflecting Optical Waveguide Couplers"; *Proceedings from SPIE, Photonics West 2003* (Jan. 25-31, 2003); vol. 4969; Laser Resonators and Beam Control VI; Item 4969-30; pp. 11-22.

Tien, P, et al, "Novel Metal-clad Optical Components and Method of Isolating High-index Substrates for Forming Integrated Optical Circuits", *Appl. Phys. Lett.*, vol. 27, No. 4, Aug. 15, 1975, pp. 251-253.

Tortorello, M.L., et al; "Antibody-Direct Epifluorescent Filter Technique for Rapid, Direct Enumeration of *Escherichia coli* O157:H7 in Beef", *Applied and Environmental Microbiology* (Oct. 1994); vol. 60, No. 10; pp. 3553-3559.

Tortorello, M.L., et al; "Rapid Identification of *Escherichia coli* O157:H7 in Bovine Feces Using the Antibody-Direct Epifluorescent Filter Technique (Ab-DEFT)", *Veterinary Microbiology* (1996); vol. 51; pp. 343-349.

Vernooy, D.W., et al; "High-Q Measurements of Fused-Silica Microspheres in the Near Infrared", *Optics Letters* (Feb. 15, 1998); vol. 23, No. 4; pp. 247-249.

Vollmer, F., et al; "Protein Detection by Optical Shift of a Resonant Microcavity", *Applied Physics Letters* (May 27, 2002); vol. 80, No. 21; pp. 4057-4059.

Yoneyama et al., "Nonradiative Dielectric Waveguide Circuit Components", *International Journal of Infrared and Millimeter Waves*, vol. 4, No. 3 (1983), p. 439-449.

Yunfeng et al., "Chemical sensors based on hydrophobic porous sol-gel films and ATR-FTIR spectroscopy", Sensors and Actuators B, Elsevier Sequoia S.A., vol. B36, No. 1, 2, and 3, Oct. 1996, pp. 517-521.

Xu, G.; "Gram Stain", University of Pennsylvania Health System [on line]; [available on the internet on Oct. 31, 1997]; [retrieved from the internet on Dec. 15, 2004]; URL <http://www.uphs.upenn.edu/bugdrug/antibiotic_manual/gram.htm>; pp. 10.

\* cited by examiner

DIELECTRIC MICROCAVITY FLUOROSENSORS EXCITED WITH A BROADBAND LIGHT SOURCE

CROSS REFERENCE TO RELATED APPLICATIONS

This application is a continuation of U.S. application Ser. No. 10/854,911, filed May 27, 2004, now U.S. Pat. No. 7,271,379 the disclosure of which is incorporated by reference in their entirety herein.

FIELD OF THE INVENTION

The invention is directed generally to optical devices, and more particularly to optical sensors that use microresonators.

BACKGROUND

Dielectric microspheres have recently drawn increasing attention as fluorosensors in sensing applications. In those sensors, the sensor surface is immobilized with a layer of molecules, such as antibodies, for the subsequent capture of analytes, such as antigens. In a direct assay configuration, antigens are conjugated with fluorescent dye molecules: when the antigen binds with the antibody on the sensor surface, the fluorescent molecule is held sufficiently close to the microsphere surface that it is excited by evanescent light circulating in the microsphere. In a sandwich-type configuration, the antigen is first bound to the antibody on the sensor surface, and then a second layer of antibodies, labeled with a fluorescent dye, is added to bind to the captured antigens. The fluorescent molecules bound to the second layer of antibodies are excited by the evanescent field arising from light propagating in the whispering gallery modes (WGMs) of the microsphere. The resulting fluorescence from the excited dyes is collected and used as an indicator of the antigen binding events.

The WGMs of the microsphere are associated with a high Q-factor, and so the intensity of light, when coupled into the WGMs, is enhanced, as compared to the input light. The degree of enhancement is proportional to the Q-factor. A narrow bandwidth, tunable semiconductor diode laser, having a sub-megahertz spectral linewidth, is typically used as the light source for exciting a WGM in a microsphere cavity. The bandwidth of the laser light is comparable to the bandwidth of a single WGM resonance. Therefore, when the laser is tuned to a particular WGM resonance, most of the coupled light falls within the resonant bandwidth, and so there is efficient coupling into the WGM resonance. The high cost of such a laser, however, has proved to be a significant obstacle to the widespread introduction of microsphere-based sensors in many applications.

SUMMARY OF THE INVENTION

Accordingly, one particular embodiment of the invention is directed to a microresonator sensor apparatus that comprises a microcavity resonator defining equatorial whispering gallery modes (EWGMs), whose frequencies are separated by the free spectral range (FSR). The EWGMs lie in a plane perpendicular to a microcavity resonator axis. A light source is optically coupled to inject light into the microcavity resonator. The light source produces output light having an output spectrum whose bandwidth is approximately equal to or broader than the FSR of the EGWMs.

Another embodiment of the invention is directed to a method of making fluorescent measurements that comprises coupling excitation light into a first microcavity resonator. The first microcavity resonator defines equatorial whispering gallery modes (EWGMs), and the excitation light has a bandwidth sufficiently broad so as to be couplable into at least two adjacent EWGMs. One or more fluorescent materials are excited using the excitation light coupled into the first microcavity resonator. A fluorescent signal arising from fluorescence of the one or more fluorescent materials is then detected.

The above summary of the present invention is not intended to describe each illustrated embodiment or every implementation of the present invention. The figures and the detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1A:
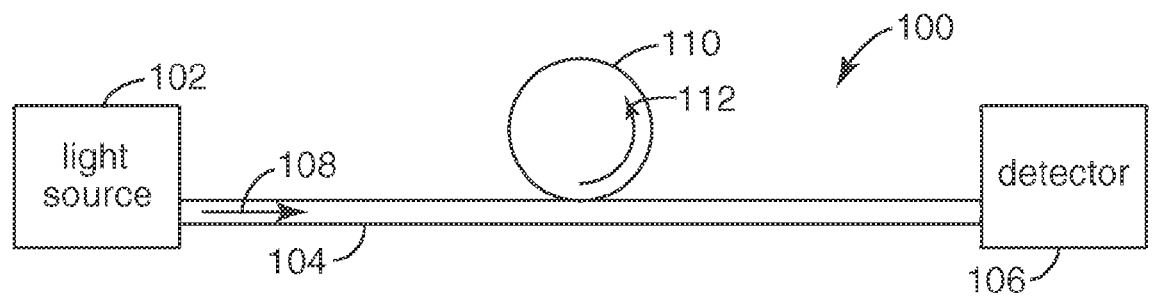
FIGS. 1A-1C schematically illustrate different embodiments of microcavity sensors according to principles of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

The present invention is particularly applicable to optical sensors that use microcavity resonators. Such resonators may also be referred to as microresonators.

In contrast to the narrow-bandwidth tunable diode laser, a semiconductor light source with a broader linewidth is relatively inexpensive. A broad bandwidth light source has heretofore been considered to be unsuitable for application with high-Q factor microspheres, because only a small portion of the output light from such a light source spectrally overlaps a single whispering gallery mode (WGM) resonance of the microsphere and can experience the enhancement afforded by the microsphere.

Broadband light sources are suitable for use with microcavities, however, when the spectral mode density of the microcavity is high and the light is coupled into multiple WGMs. Under such conditions, a significant fraction of the output from the broadband source can be coupled into the microcavity, and so the combination of a broadband light source and microcavity leads to a fluorosensor having high sensitivity with low associated component cost.

An example of a microcavity-waveguide system 100 that uses a microresonator is schematically illustrated in FIG. 1A. A light source 102 directs light along a waveguide 104 to a detector unit 106. The microresonator 110 is optically coupled to the waveguide 104. Light 108 from the light source 102 is launched into the waveguide 104 and propagates towards the detector unit 106. The microresonator 110 evanescently couples some of the light 108 out of the waveguide 104, the out-coupled light 112 propagating within the microresonator 110 at one of the resonant frequencies of the microresonator 110.

The light source 102 may be any suitable type of light source. For increased efficiency and sensitivity, it is advantageous that the light source produces light that is efficiently coupled into the waveguide 104, for example the light source may be a laser such as a laser diode, or may be a light emitting diode. The light source 102 generates light 108 at a desired wavelength, or wavelength range. For example, where the microresonator is used in a sensor, the light source 102 generates light at a wavelength that interacts with the species being sensed. The species being sensed is typically located in proximity to the surface of the microresonator 110 so that the light propagating in the WGM interacts with the species being sensed. The light source 102 may also comprise a lamp, along with suitable optics for coupling light from the lamp into the waveguide 104.

For example, when the system 100 is used as a fluorosensor, the light propagating within the microresonator 110 is absorbed by a fluorescent molecule, such as a fluorescent dye, that is attached on the microresonator surface to an analyte or to a marker that indicates the presence of the analyte. In a more specific example, the surface of the microresonator may be attached with antibodies specific to a desired antigen analyte. The analyte antigen molecules, conjugated with a fluorescent dye, are introduced to the sensor system 100. The antigen molecules bind to the antibody molecules on the microresonator 110, thus holding the fluorescent dye molecules sufficiently close to the microresonator 110 that the light circulating within microresonator 110 evanescently couples to the fluorescent molecules. The absorbed light excites the fluorescent molecules and the molecules subsequently fluoresce at a wavelength different from the excitation wavelength. Detection of the fluorescent light confirms the presence of the analyte antigen.

In another example, the analyte antigen molecules are not conjugated with a fluorescent dye, but are allowed to bind to the antibodies attached to the microresonator surface. More antibodies, conjugated to fluorescent molecules, are subsequently introduced to the sensor, and bind to the antigen. Again, the fluorescent molecules are excited by an evanescent interaction with the light propagating within the microresonator 110, and detection of the subsequent fluorescence may be used to determine the presence and abundance of the analyte antigen.

The light source 102 may direct light into a number of different waveguides, of which the waveguide 104 is one such example The waveguide 104 may be any suitable type of waveguide and may be, for example, a planar waveguide or a channel waveguide formed in or on a substrate, such as a waveguide formed in a silica substrate. The waveguide 104 may also be an optical fiber.

The detector unit 106 includes a light detector, for example a photodiode or phototransistor, to detect light. The detector unit 106 may also include a wavelength sensitive device that selects the wavelength of light reaching the light detector. The wavelength selective device may be, for example, a filter, or a spectrometer. The wavelength selective device may be tunable so as to permit the user to actively change the wavelength of light incident on the light detector.

The microresonator 110 may be positioned in physical contact with, or very close to, the waveguide 104 so that a portion of the light 108 propagating along the waveguide 104 is evanescently coupled into the microresonator 110. The waveguide 104 typically has little or no cladding at the point where the microresonator 110 couples to the waveguide 104, so that the microresonator 110 couples directly to the core of the waveguide 104.

Figure 1B:
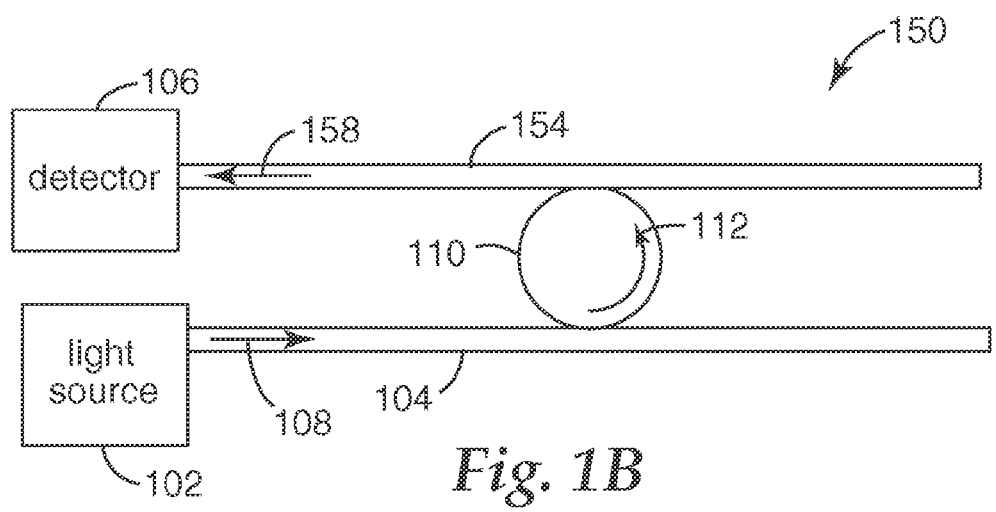

Another type of microresonator device 150 is schematically illustrated in FIG. 1B. In this device 150, light 158 from the microresonator 110 is coupled into a second waveguide 154, and propagates to the detector 106.

Figure 1C:
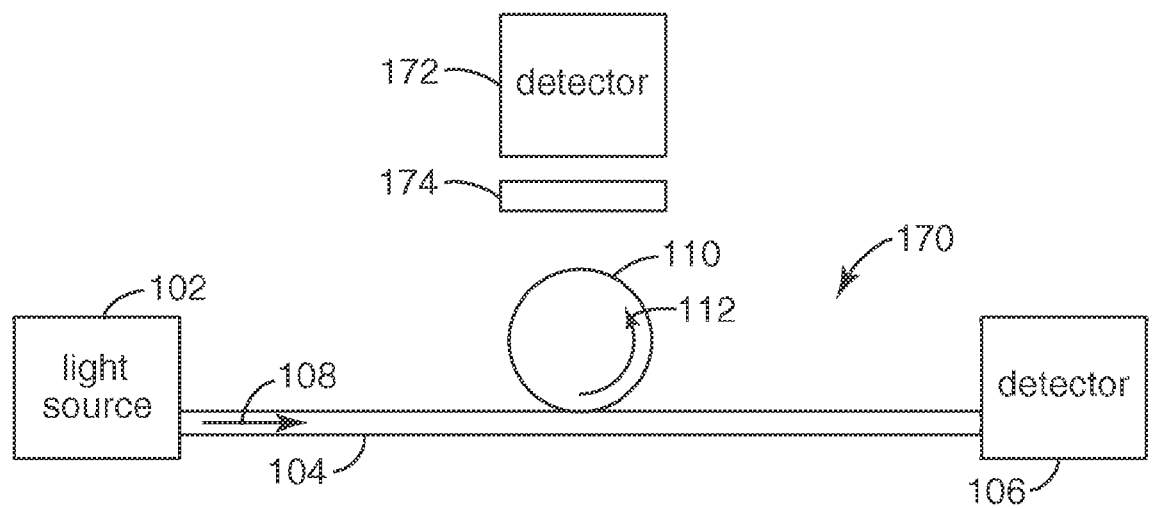

Another type of microresonator device 170 is schematically illustrated in FIG. 1C. In this device 170, a second detector 172 is positioned close to the microresonator 110 to detect light from the microresonator 110. The light detected by the second detector 172 does not pass to the second detector 172 via a waveguide, and is said to propagate through free space. The light from the microresonator 110 that is detected by the second detector 172 may be, for example, scattered out of the microresonator 110 or may be fluorescent light arising from excitation of a fluorescent species, attached to the surface of the microresonator, by light circulating within the microresonator 110. The second detector 172 may detect all wavelengths of light from the microresonator 110 or, for example through the use of a wavelength selective element 174 placed between the second detector 172 and the microresonator 110, may detect light that lies in a specific wavelength range. The wavelength selective element 174 may, for example, be a filter that rejects light at the excitation wavelength resonating within the microresonator 110 and that transmits light at the fluorescent wavelength. The second detector 172 may also be used with a configuration like that shown in FIG. 1B.

Figure 2:
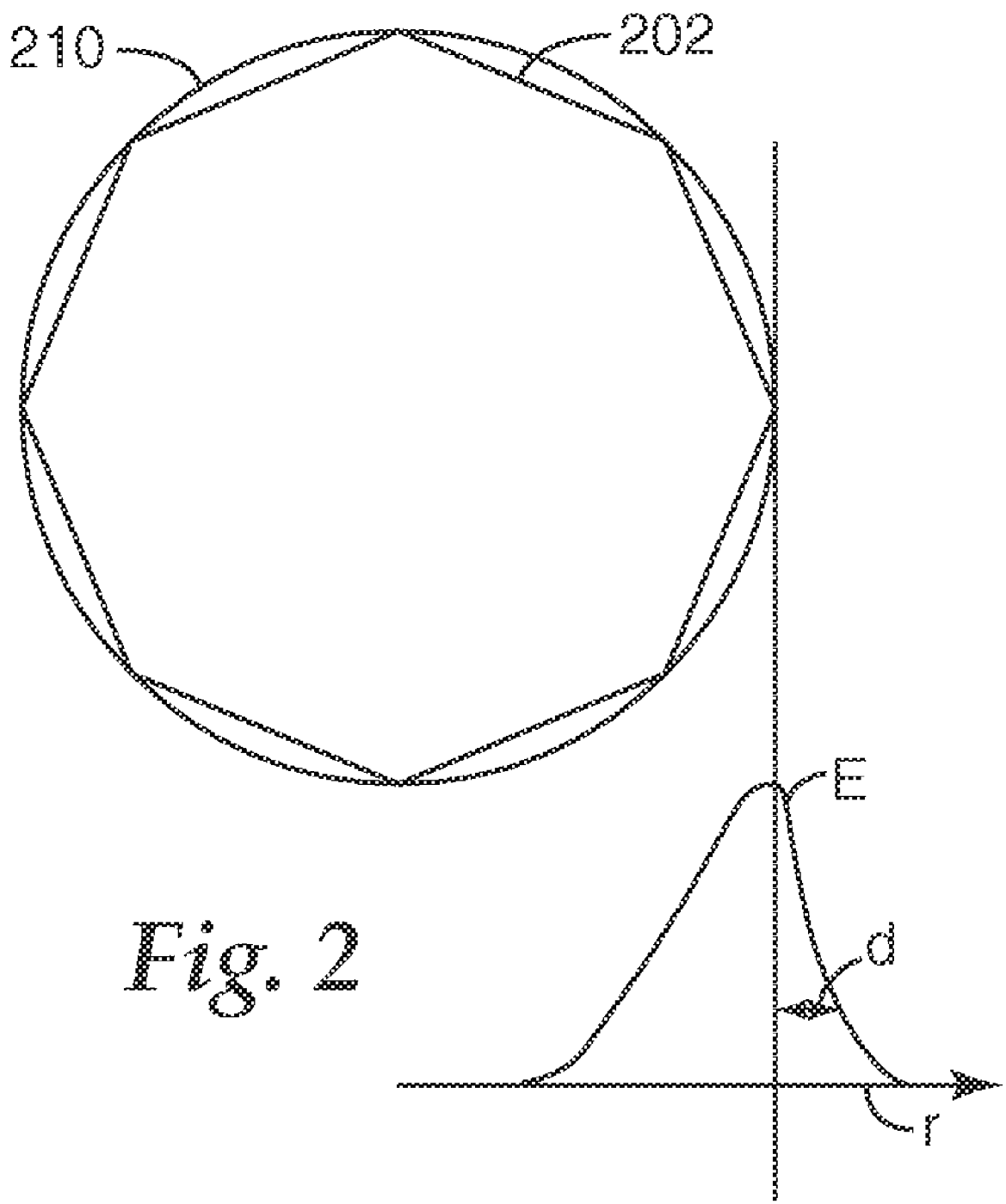
FIG. 2 schematically illustrates whispering gallery modes in a microcavity resonator.

Light propagates within the microresonator in so-called "whispering gallery modes", an example of which is schematically illustrated in FIG. 2. In a whispering gallery mode (WGM) 202, the light propagates around the microresonator 210 from an origin via a number of total internal reflections, until it returns to the origin. In the illustrated embodiment, the WGM 202 includes eight total internal reflections in a single round trip. It will be appreciated that the light may propagate within the microresonator 210 in other WGMs that correspond to different numbers of total internal reflections.

Furthermore, the WGM 202 only demonstrates a high Q-factor where the light is of such a wavelength that it constructively interferes after one round trip. Stated another way, the optical path length around the WGM 202 is equal to an integral number of wavelengths. This resonant condition for light in the planar WGM 202 illustrated in FIG. 2 can be stated mathematically as:

$$l\lambda_l = L \qquad (1)$$

where $\lambda_l$ is the wavelength of the lth mode in vacuum, L is the optical length of one round trip of the WGM, and l is an integer, referred to as the mode number. Light from the waveguide 104 that satisfies the resonant condition (1) is efficiently coupled to the microresonator. The resonant modes of microcavities are described further in, for example, "Theory of morphology-dependent resonances: shape resonances and width formulas", B. R. Johnson, *Journal of the Optical Society of America A,* vol. 10, pages 343-352, (1993), and "Mapping whispering-gallery modes in microspheres with a near-field probe", J. C. Knight et al., *Optical Letters,* vol. 20, pages 1515-1517 (1995).

The electric field intensity of the WGM peaks at the interior surface of the microresonator 210. The electric field intensity of the WGM decays exponentially outside the microresonator 210, with a characteristic decay length, d, given approximately by d≈λ/n where λ is the wavelength of the light in vacuum and n is the refractive index of the medium outside the microresonator 210. The field intensity, E, is schematically illustrated in FIG. 2 for the WGM 202 along the cross-section line AA'.

The microresonator 210 typically has a diameter in the range from 20 μm to a few millimeters, but is more often in the range 50 μm-500 μm. Furthermore, the waveguide is often tapered to increase the intensity of the optical field intensity outside the waveguide, thus increasing the amount of light that couples into the microresonator. In the case of an optical fiber waveguide, the fiber may be heated and tapered or etched to a total thickness of about 1-5 μm. Likewise, with a planar or channel waveguide, the waveguide thickness may be reduced at the region where the light is coupled to the microresonator. In addition to the waveguide being reduced in size, the thickness of the cladding around the waveguide may also be reduced. Various approaches to coupling the microresonator to a waveguide or fiber are discussed in greater detail in commonly owned and co-pending U.S. patent application Ser. No. 10/685,049, incorporated herein by reference.

Different types of microcavity resonators are now described with reference to FIGS. 3A-4C. Each of the WGMS 306, 316 and 326 shown in FIGS. 4A-4C corresponds to a WGM having only a single number of total internal reflections.

Figure 3A:
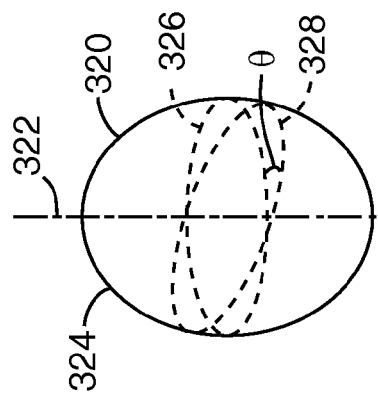
FIGS. 3A-3C schematically illustrate cylindrical, spherical and bulge-like microcavities respectively.

FIG. 3A schematically illustrates a cylindrical microresonator 300, with a longitudinal axis 302 that lies parallel to the circular walls 304 of the cylindrical microresonator 300. Such a microresonator may be formed, for example, using an optical fiber, where light is coupled tangentially into the side of the fiber, in a direction perpendicular to the fiber axis. The WGM 306 is shown in dashed lines, lying in a plane that is perpendicular to the axis 302. The cylindrical microresonator 300 does not support WGM modes that lie in a plane non-perpendicular to the axis, since such light does not follow a closed path and escapes from the resonant cavity. Because the WGM 306 lies in a plane perpendicular to the axis 302, the WGM may be referred to as an equatorial WGM (EWGM).

Figure 4A:
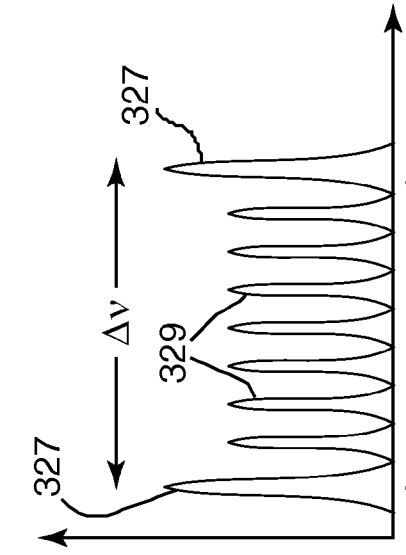
FIGS. 4A-4C schematically present portions of the resonant spectra of the microcavities illustrated in FIGS. 3A-3C respectively.

Accordingly, the resonant spectrum of the EWGM 306 is like that shown in FIG. 4A, which shows the resonances plotted as a function of frequency, υ. The lth resonant mode is separated from the (l+1)th resonant mode by a separation equal to Δυ, also referred to as the free spectral range (FSR), where Δυ corresponds to an increase of one in the number of wavelengths around the EWGM 306. The FSR may be calculated in terms of frequency according to the following expression:

$$FSR = \Delta\upsilon = c/L \approx c/(\pi n D) \qquad (2)$$

where c is the speed of light in vacuum, n is the refractive index of the microcavity, D is the cylinder diameter, and nπD approximates the optical length of one round trip of the EWGM. The lth and (l+1)th mode are referred to as adjacent EGWM modes.

Note that FSR can also be expressed in terms of wavelength:

$$FSR \text{ (in wavelength)} = \Delta\upsilon\lambda^2/c = \lambda^2/(\pi n D) \qquad (3)$$

where λ is the wavelength of light in vacuum. Both definitions of FSR are used here interchangeably.

Other EWGMs have different numbers of total internal reflections and, therefore, have optical path lengths different from that of the mode shown. The resonant frequencies associated with these other EGWMs are different from the resonant frequencies shown in FIG. 4A.

Figure 3B:
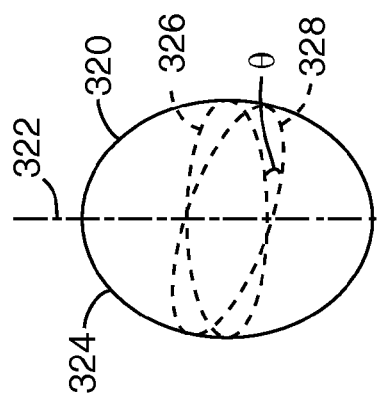

FIG. 3B schematically illustrates a spherical microresonator 310 positioned on an axis 312. Such a microresonator may be formed, for example, using a glass sphere having a spherical wall 314. The EWGM 316 is shown, in dashed lines, lying in a plane perpendicular to the axis 312. The resonant spectrum of the EWGM 316 is schematically illustrated in the graph shown in FIG. 4B. Like the EWGM 306 of the cylindrical resonator, the frequency spacing between adjacent resonances is given by Δυ (FSR), where Δυ corresponds to an increase of one in the number of whole integer wavelengths around the EWGM 316. The FSR is given by expression (2) above, where D is the diameter of the spherical microresonator 310.

Unlike the planar microresonator, however, the spherical microresonator 310 does support WGMs that do not lie perpendicular to the axis 312. One such WGM 318 is shown (in dashed lines) that lies at an angle, θ, relative to the WGM 316. The WGM 318 is referred to as a non-equatorial mode, or azimuthal mode. Since the microresonator 310 is spherical, however, the path length of the WGM 318 is identical to the path length of the EWGM 316, and so the resonant frequencies for the WGM 318 are identical to those for EWGM 316. Since the frequency of the non-equatorial modes is the same as the EWGM, the non-equatorial modes are said to be degenerate in frequency.

Figure 4B:
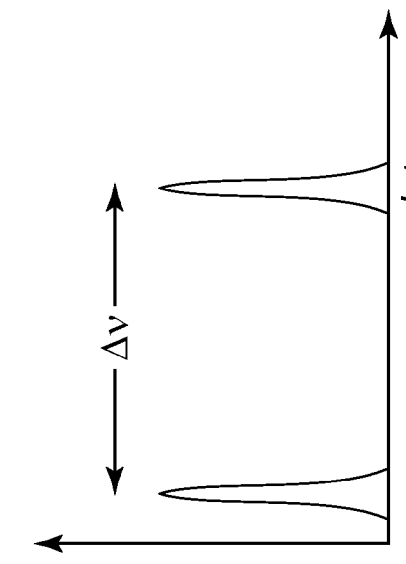

Other resonant spectra, corresponding to EWGMs having different numbers of total internal reflections, have resonant frequencies different from the resonant frequencies shown in FIG. 4B.

Figure 3C:
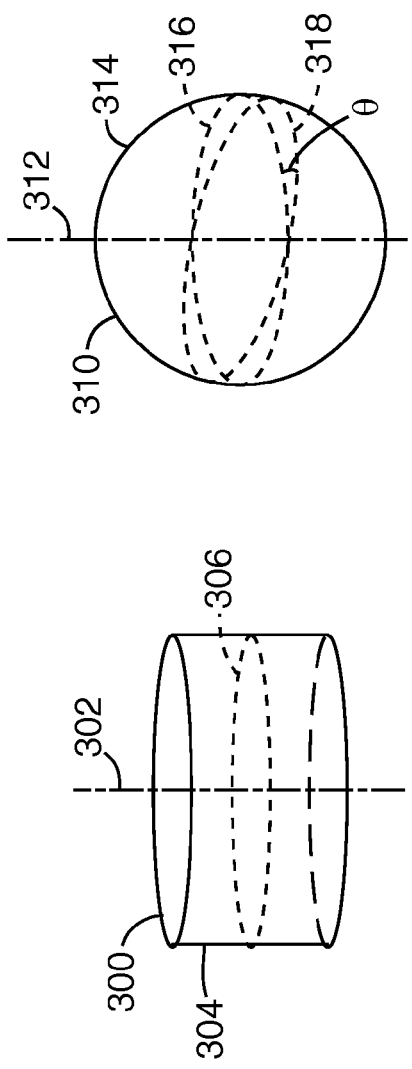

FIG. 3C schematically illustrates a microresonator 320 that is neither cylindrical, nor spherical. In the illustrated embodiment, the microresonator 320 has an ellipsoidal wall 324. The microresonator 320 is positioned on an axis 322. An EWGM 326 is shown in dashed lines lying in a plane perpendicular to the axis 322. Some of the resonances of the equatorial EWGM 326 are schematically shown as resonances 327 in the graph shown in FIG. 4C. The frequency spacing between adjacent resonances 327 of the EWGM 326 is given by Δυ (FSR), where Δυ corresponds to an increase of one in the number of whole integer wavelengths around the EWGM 326. The FSR is given by expressions (2) and (3) above, where nπD approximates the optical path length of one round trip of the EWGM.

Figure 4C:
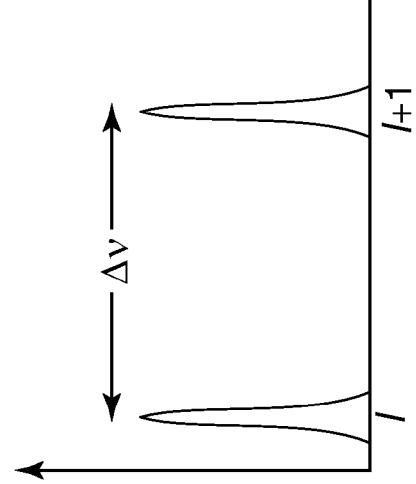

When the optical path of a mode is tilted through an angle, θ, from zero, to form a non-equatorial path, the resonances associated with the non-equatorial path are not the same as those for the equatorial mode, however. This is because the path length around the elliptical microresonator varies when θ is increased from zero. In other words, the path length for the equatorial mode is different from that of the non-equatorial mode. Thus, different non-equatorial WGMs have different resonant frequencies that vary with values of θ. Thus, the resonance spectrum for the microresonator 320 contains many resonances 329 for non-equatorial modes that "fit-in" to the regions between resonances 327 of the equatorial modes. Note that only a few of the non-equatorial resonances have been included in FIG. 4C, and the representation of non-equatorial resonances 329 in FIG. 4C is given only for qualitative purposes. The magnitudes of the non-equatorial resonances 329 are shown in FIG. 4C to be less than the magnitudes of the equatorial resonances 327 for purposes of distinguishing between equatorial and non-equatorial resonances. There is no intention, however, to indicate that the non-equatorial resonances 329 have a different Q-factor from the equatorial resonances 327. In such a case, when a broadband light source is used, the total light intensity in the microcavity is enhanced by a factor proportional to the number of modes that fit into one FSR.

One type of microcavity resonator that has a broad range of cavity resonance frequencies is the bulge-like microcavity, described in greater detail in DIELECTRIC MICROCAVITY SENSORS, filed on even date herewith by X. Fan and R. Wilson, and having U.S. application Ser. No. 10/855,462, incorporated herein by reference.

Figure 5A:
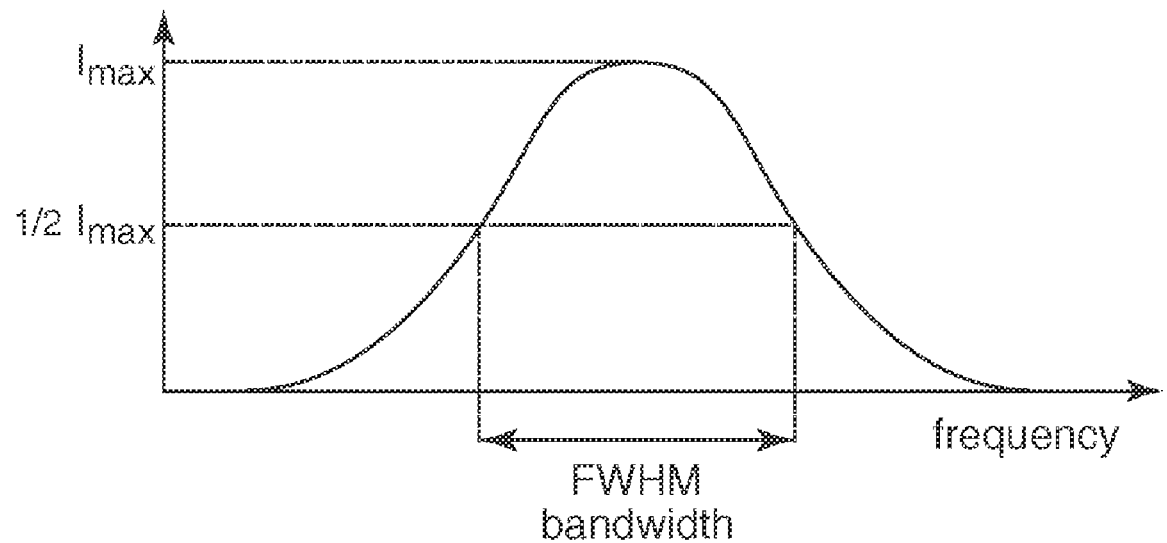
FIG. 5A shows the bandwidth of an exemplary light source.
Figure 5B:
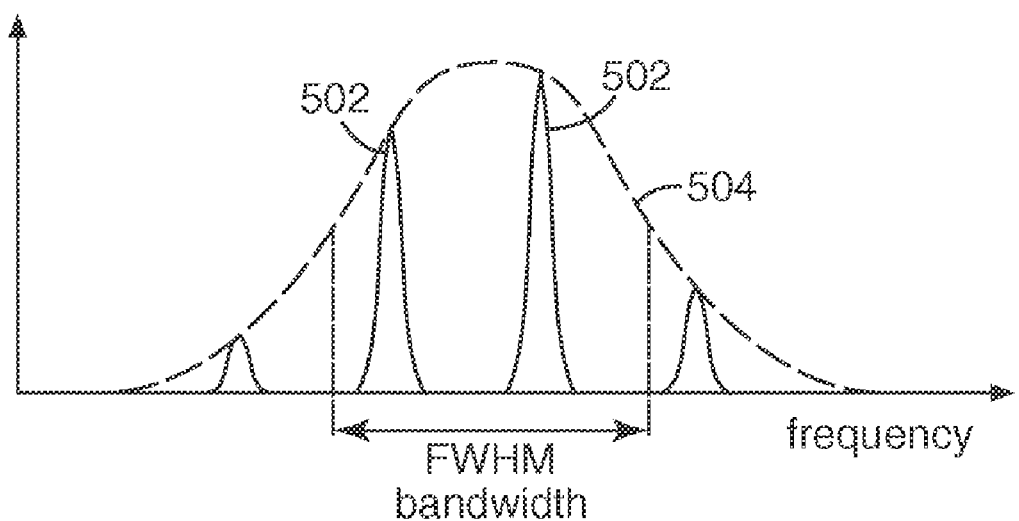
FIG. 5B shows the bandwidth of a light source that emits light into resonant modes.

The light that is coupled into the microcavity may have a relatively broad spectrum and, for example, may be approximately equal to or greater than the FSR of the EWGM of the microcavity, Δυ. The bandwidth of the light is typically measured as its full width, half maximum (FWHM) bandwidth, see FIG. 5A. Where the light is generated in a laser, the light spectrum may comprise a number of discrete modes 502, corresponding to the Fabry-Perot resonances of the laser, that lie within an amplitude envelope 504: see the schematic illustration in FIG. 5B. In such a case, the bandwidth of the light is the FWHM bandwidth of the envelope 504.

In a conventional cylindrical microresonator, the coupling of light from the waveguide to the microresonator is sensitive to the alignment between the waveguide and the microresonator: if the light is not injected into the equatorial mode of the microresonator, then the light may enter a low Q mode and be quickly lost. The coupling of light is less sensitive to the alignment of a bulge-like cavity relative to the waveguide, however, since the bulge-like cavities provide light confinement in three dimensions, and not just two as with a cylindrical microcavity. Furthermore, even though the cylindrical microcavity may have a large lateral extent, along the cylindrical axis, for example when formed from an optical fiber, the waveguide that couples light into the cylindrical microcavity is typically relatively narrow. Relatively wider waveguides support greater numbers of transverse modes, thus increasing the possibility that light from the waveguide will enter into a non-equatorial WGM of the cylindrical microcavity and be lost. Wider waveguides may be used with bulge-like microcavities, however, since the three dimensional confinement properties of the bulge-like microcavity permits the efficient excitation of non-equatorial modes that have a high Q. The use of wider waveguides may lead to an improved optical coupling efficiency for light between the light source and the waveguide and between the waveguide and the microcavity.

Thus, the use of a microresonator that is not cylindrical leads to the presence of cavity resonances having many more different values of resonant frequency than a cylindrical microcavity. In addition, a microcavity that is not spherical does not show the same frequency degeneracy as a spherical microcavity. As a result, a non-spherical microcavity (having non-equatorial modes with non-degenerate frequencies) results in an increase in the number of different frequencies at which resonance can take place. Such a microcavity resonator can demonstrate the existence of higher numbers of resonances per unit frequency as compared with the cylindrical or spherical microresonators of FIGS. 3A and 3B. However, it is difficult to obtain a microcavity that is perfectly spherical, and even a small non-sphericity in the microcavity results in a breaking of the degeneracy. Thus, light from a broadband light source may effectively be coupled into multiple cavity resonant modes. Examples of broadband light sources include light emitting diodes and semiconductor lasers, such as a semiconductor laser having a Fabry-Perot cavity. Such broadband light sources are considerably less costly than tunable semiconductor lasers that produce light with an output bandwidth of less than 1 MHz. Thus, in one exemplary embodiment, light may be supplied by the light source having a bandwidth that is approximately the same as, or greater than, one FSR of an EGWM of the microresonator. In another exemplary embodiment, the bandwidth of the light may be more than five time the FSR, and in another exemplary embodiment, may be more than ten times the FSR.

EXAMPLE

An experiment was performed in which the illumination with a frequency-narrowed, tunable semiconductor diode laser was compared with the illumination using a broadband source. The experimental setup was similar to that illustrated in FIG. 1C, in which the light source directed light in the range of 630-635 nm through a tapered fiber as the coupling waveguide. The fiber core tapered to a diameter of around 1.5 μm-2.5 μm. A first detector was positioned to detect light that had passed along the waveguide, past the microcavity. A second detector was positioned to detect the free space emission of light from the microcavity.

A glass microcavity was formed with a diameter of about 150 μm by melting the tip of a SFM28 optical fiber with a $CO_2$ laser. The glass microcavity was close to being spherical and was attached with biotinated bovine serum albumin (BSA). A sample of streptavidin was labeled with Alexa Fluor 647 as a fluorophore. The streptavidin sample, having a concentration of 800 pM (50 ng/ml) was introduced to the microcavity. The streptavidin bound to the biotin on the microcavity surface, thus binding the fluorophore to the micro cavity.

Figure 6:
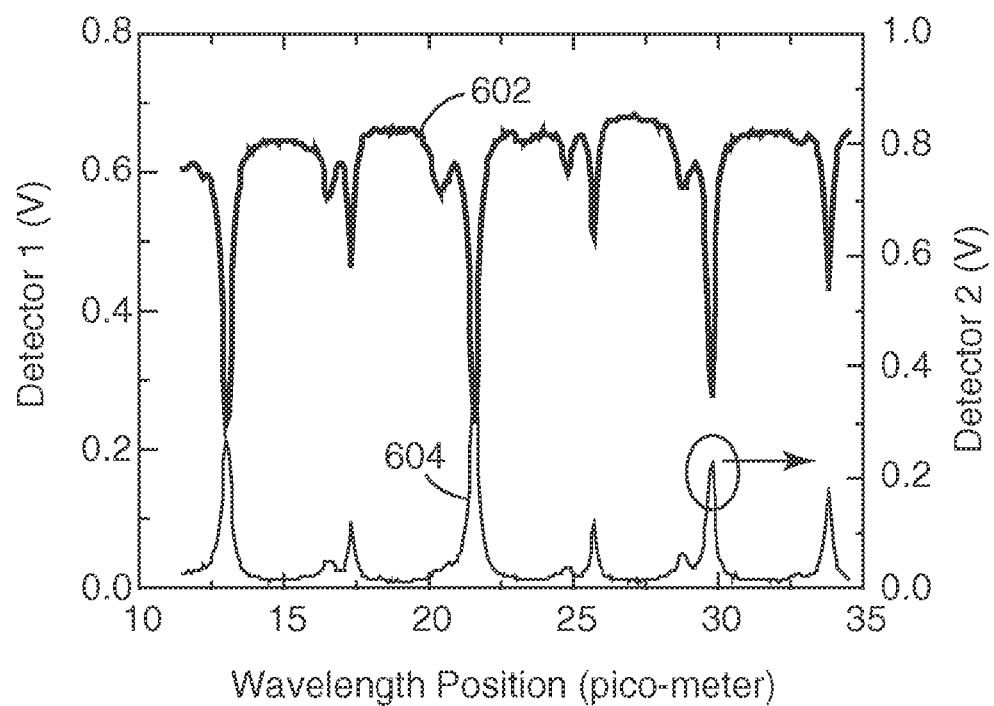
FIG. 6 shows resonant spectra of a microcavity as measured using narrowband light from a tunable semiconductor laser.
Figure 7:
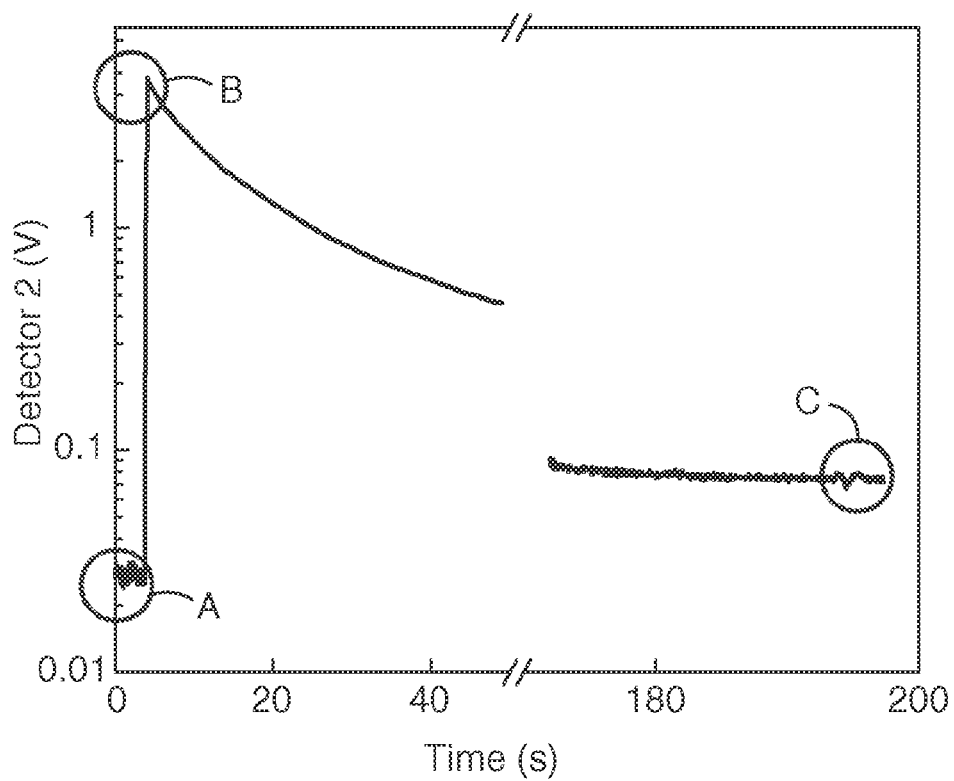
FIG. 7 shows the temporal dependence of a fluorescent signal obtained from a microcavity when excited with broadband light.

The microcavity was first illuminated with light coupled from a tunable semiconductor laser, tunable over the range of at least 630 nm-633 nm. FIG. 6 shows the spectra obtained from the two detectors when the laser was scanned over a range of about 25 pm. The upper curve, labeled 602, corresponds to the signal detected by the first detector. The dips in the detection signal correspond to resonances of the microcavity. The free spectral range (FSR) of the microcavity was calculated using expression (3):

$$FSR \text{ (in wavelength)} = \Delta\upsilon\lambda^2/c = \lambda^2/(\pi nD) \qquad (3)$$

where c is the speed of light in vacuum, λ is the wavelength of the light in vacuum, n is the refractive index of the microcavity and D approximates the diameter of the nearly spherical microcavity. For the microcavity used in the experiments, the FSR was approximately 580 pm.

The lower curve, labeled 604, corresponds to the free space fluorescent signal detected by the second detector located close to the microcavity. The fluorescent peaks of curve 604 correspond to excitation of the fluorophore at the resonant frequencies of the microcavity.

In the next experiment, a microcavity having a diameter of about 250 μm, with a concomitant FSR of about 350 pm, was illuminated using light from a laser diode that had an output at 635 nm and an output bandwidth of 0.5 nm (500 pm). In this particular example, the bandwidth of the light output from the laser is greater than a single FSR. The optical power coupled into the fiber taper was approximately 250 μW.

A streptavidin sample, having a concentration of 8 pM, (500 pg/ml) was introduced to the surface of the microcavity. The response of the second detector, which detected the free-space fluorescent signal, is provided in the graph in FIG. 6 as a function of time. The excitation light was initially blocked at the input to the tapered fiber, so that no light was coupled into the microcavity, point A. Accordingly, the signal level at point A, approximately 0.03 V, corresponds to the level of background noise in the signal from the second detector.

When the excitation light was unblocked at point B, a strong fluorescent signal was observed. This corresponds to the fluorophore emitting light as a result of being excited by light resonant in the microcavity. The signal at point B is approximately 3V, and so the signal-to-noise ratio was about 100. The light from the laser diode was chopped and the fluorescent signal detected using a lock-in amplifier.

After approximately 180-200 sec of excitation time, the fluorescent signal had fallen to a level of about 0.08 V. This reduction in signal strength over time was attributed to bleaching of the dye molecules.

These experimental results demonstrate the detection of Streptavidin (labeled with Alexa Fluor 647) with a concentration as low as 8 pM (500 pg/ml), where the light source had a bandwidth of more than the FSR of the microcavity. The detection limit is estimated to be approximately 80 fM (5 pg/ml), everything else being equal. It is expected that, when the fluorosensor is incorporated with a fluidic system for a more efficient sample delivery, an even lower detection limit may be achieved.

The experiment described above shows that broadband light sources, instead of tunable, narrowband sources, can effectively be used in fluorosensing measurements. The use of broadband light sources, for example, light sources whose output light has a bandwidth greater than the free spectral range of a WGM, may lead to a significant reduction in the component cost of microcavity fluorosensor systems.

Accordingly, the present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the present specification. The claims are intended to cover such modifications and devices.

We claim:

1. A microresonator apparatus, comprising:
   a microcavity resonator capable of supporting multiple resonant modes;
   a light source optically coupled to the microcavity resonator and capable of simultaneously exciting the multiple resonant modes;
   a fluorescent material optically coupled to the microcavity resonator;
   a first detector disposed to detect light from the microcavity resonator; and
   a second detector disposed to detect fluorescent light produced by the fluorescent material.

2. The microresonator apparatus of claim 1, wherein the multiple resonant modes comprise at least two whispering gallery modes (WGMs).

3. The microresonator apparatus of claim 2, wherein the at least two WGMs comprise at least two adjacent WGMs.

4. The microresonator apparatus of claim 2, wherein the at least two WGMs comprise at least two equatorial whispering gallery modes (EWGMs).

5. The microresonator apparatus of claim 1, wherein the light source is optically coupled to the microcavity resonator via an optical waveguide.

6. The microresonator apparatus of claim 5, wherein the optical waveguide comprises a tapered fiber.

7. The microresonator apparatus of claim 1, wherein the light source comprises a light emitting diode.

8. The microresonator apparatus of claim 1, wherein the second detector detects the fluorescent light propagating in free space from the fluorescent material.

9. The microresonator apparatus of claim 1 further comprising an analyte optically coupled to the microcavity resonator and the fluorescent material.

10. The microresonator apparatus of claim 1, wherein the multiple resonant modes comprise at least five resonant modes.

11. The microresonator apparatus of claim 1, wherein the multiple resonant modes comprise at least ten resonant modes.

* * * * *

UNITED STATES PATENT AND TRADEMARK OFFICE
CERTIFICATE OF CORRECTION

PATENT NO. : 7,622,705 B2  
APPLICATION NO. : 11/843917  
DATED : November 24, 2009  
INVENTOR(S) : Xudong Fan It is certified that error appears in the above-identified patent and that said Letters Patent is hereby corrected as shown below:

Column 7

Line 23; After "having" insert -- attorney docket no. 59632US002, --.

Column 8

Line 44; Delete "micro cavity." and insert -- microcavity. --, therefor.

Line 56; Delete " $\lambda$is" and insert -- $\lambda$ is --, therefor.

Signed and Sealed this

First Day of June, 2010

David J. Kappos
*Director of the United States Patent and Trademark Office*